United States Patent [19]

Morozowich

[11] 4,207,257

[45] Jun. 10, 1980

[54] INTER-PHENYLENE-13,14-DIHYDRO-PG AMIDES

[75] Inventor: Walter Morozowich, Kalamazoo Township, Kalamazoo County, Mich.

[73] Assignee: The Upjohn Company, Kalamazoo, Mich.

[21] Appl. No.: 898,251

[22] Filed: Apr. 20, 1978

Related U.S. Application Data

[63] Continuation-in-part of Ser. No. 788,455, Apr. 18, 1977, Pat. No. 4,100,192.

[51] Int. Cl.$^2$ .................. C07C 103/22; C07C 103/76
[52] U.S. Cl. ........................... 260/558 R; 260/558 P; 260/559 R; 260/559 P
[58] Field of Search ........... 260/558 R, 558 P, 559 R, 260/559 B

[56] References Cited

U.S. PATENT DOCUMENTS

| | | | |
|---|---|---|---|
| 3,933,895 | 1/1976 | Nelson | 260/473 A |
| 3,933,897 | 1/1976 | Nelson | 260/473 A |
| 3,933,898 | 1/1976 | Nelson | 260/473 A |
| 3,933,899 | 1/1976 | Nelson | 260/473 A |
| 3,933,900 | 1/1976 | Nelson | 260/473 A |
| 3,981,868 | 9/1976 | Karel | 542/429 |

*Primary Examiner*—Arthur P. Demers
*Attorney, Agent, or Firm*—Robert A. Armitage

[57] ABSTRACT

The present invention relates to inter-phenylene-13,14-dihydro-PG amides. These compounds are pharmacological agents, being prolonged orally active platelet aggregation inhibitors in mammalian species. These compounds are accordingly useful for antithrombotic applications.

43 Claims, No Drawings

INTER-PHENYLENE-13,14-DIHYDRO-PG AMIDES

This application is a continuation-in-part of Ser. No. 788,455, filed Apr. 18, 1977, now U.S. Pat. No. 4,100,192, issued July 11, 1978.

SPECIFICATION

The present invention relates to inter-phenylene-13,14-dihydro-PG amides, the essential material constituting a disclosure of which is incorporated here by reference from Ser. No. 788,455. In particular, the present invention relates to inter-phenylene-13,14-dihydro-PG amides of the unsubstituted inter-phenylene PG amides described in Ser. No. 788,455 now U.S. Pat. No. 4,100,192.

I claim:

1. A prostaglandin analog of the formula

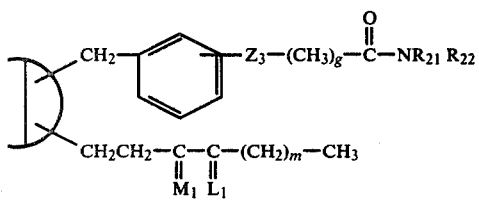

wherein D is

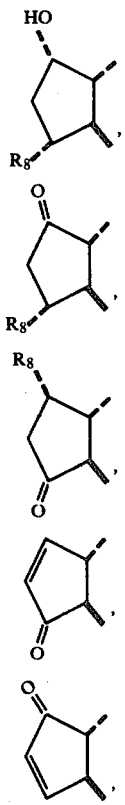

wherein $R_8$ is hydrogen or hydroxy;
wherein g is one, 2, or 3;
wherein $Z_3$ is oxa or methylene;
wherein $L_1$ is

or a mixture of

and

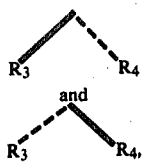

wherein $R_3$ and $R_4$ are hydrogen, methyl, or fluoro, being the same or different, with the proviso that one of $R_3$ and $R_4$ is methyl only when the other is hydrogen or methyl;

wherein $M_1$ is

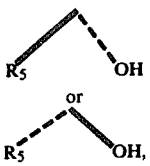

wherein $R_5$ is hydrogen or methyl;
wherein m is one to 5, inclusive; and
wherein $R_{21}$ and $R_{22}$ are
  (i) hydrogen;
  (ii) alkyl of one to 12 carbon atoms, inclusive;
  (iii) cycloalkyl of 3 to 10 carbon atoms, inclusive;
  (iv) aralkyl of 7 to 12 carbon atoms, inclusive;
  (v) phenyl;
  (vi) phenyl substituted with one, 2, or 3 chloro, alkyl of one to 3 carbon atoms, inclusive, hydroxy or nitro;
  (vii) hydroxylalkyl of one to 4 carbon atoms, inclusive;
  (viii) dihydroxyalkyl of one to 4 carbon atoms; or
  (ix) trihydroxyalkyl of one to 4 carbon atoms;
with the further proviso that not more than one of $R_{21}$ and $R_{22}$ is other than hydrogen or alkyl.

2. A prostaglandin analog according to claim 1, wherein D is

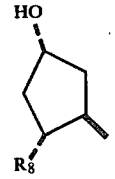

3. A prostaglandin analog according to claim 2, wherein $R_8$ is hydrogen.

4. 3,7-inter-m-Phenylene-3-oxa-4,5,6-trinor-13,14-dihydro-11-deoxy-PGF$_1$, amide, a prostaglandin analog according to claim 3.

5. A prostaglandin analog according to claim 2, wherein $R_8$ is hydroxy.

6. 3,7-inter-m-Phenylene-3-oxa-4,5,6-trinor-13,14-dihydro-11-deoxy-PGF$_1$, amide, a prostaglandin analog according to claim 5.

7. A prostaglandin analog according to claim 1, wherein D is

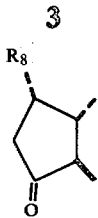

8. A prostaglandin analog according to claim 7, wherein R$_8$ is hydrogen.

9. 3,7-inter-m-Phenylene-3-oxa-4,5,6-trinor-13,14-dihydro-9-deoxy-PGD$_1$, amide, a prostaglandin analog according to claim 8.

10. A prostaglandin analog according to claim 7, wherein R$_8$ is hydroxy.

11. 3,7-inter-m-Phenylene-3-oxa-4,5,6-trinor-13,14-dihydro-PGD$_1$, amide, a prostaglandin analog according to claim 10.

12. A prostaglandin analog according to claim 1, wherein D is

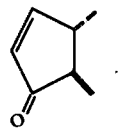

13. 3,7-inter-m-Phenylene-3-oxa-4,5,6-trinor-13,14-dihydro-9-deoxy-9,10-didehydro-PGD$_1$, amide, a prostaglandin analog according to claim 12.

14. A prostaglandin analog according to claim 1, wherein D is

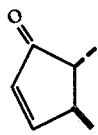

15. 3,7-inter-m-Phenylene-3-oxa-4,5,6-trinor-13,14-dihydro-PGA$_1$, amide, a prostaglandin analog according to claim 14.

16. A prostaglandin analog according to claim 1, wherein D is

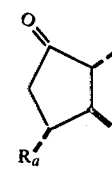

17. A prostaglandin analog according to claim 16, wherein R$_8$ is hydrogen.

18. 3,7-inter-m-Phenylene-3-oxa-4,5,6-trinor-13,14-dihydro-11-deoxy-PGE$_1$, amide, a prostaglandin analog according to claim 17.

19. A prostaglandin analog according to claim 16, wherein R$_8$ is hydroxy.

20. A prostaglandin analog according to claim 19, wherein Z$_3$ is methylene.

21. A prostaglandin analog according to claim 20, wherein Z$_3$ is attached to the phenyl ring in the position meta to methylene.

22. 3,7-inter-m-Phenylene-4,5,6-trinor-13,14-dihydro-PGE$_1$, amide, a prostaglandin analog according to claim 21.

23. A prostaglandin analog according to claim 19, wherein Z$_3$ is oxa.

24. A prostaglandin analog according to claim 23, wherein M$_1$ is

25. 15-epi-3,7-inter-m-Phenylene-3-oxa-4,5,6-trinor-13,14-dihydro-PGE$_1$, amide, a prostaglandin analog according to claim 24.

26. A prostaglandin analog according to claim 23, wherein M$_1$ is

27. A prostaglandin analog according to claim 26, wherein Z$_3$ is attached to the phenyl ring in the position meta to methylene.

28. A prostaglandin analog according to claim 27, wherein m is 3.

29. A prostaglandin analog according to claim 28, wherein g is 3.

30. 2a,2b-Dihomo-3,7-inter-m-phenylene-3-oxa-4,5,6-trinor-13,14-dihydro-PGE$_1$, amide, a prostaglandin analog according to claim 29.

31. A prostaglandin analog according to claim 28, wherein g is one.

32. A prostaglandin analog according to claim 31, wherein at least one of R$_3$ and R$_4$ is methyl.

33. 3,7-inter-m-Phenylene-3-oxa-4,5,6-trinor-16,16-dimethyl-13,14-dihydro-PGE$_1$, amide, a prostaglandin analog according to claim 32.

34. A prostaglandin analog according to claim 31, wherein at least one of R$_3$ and R$_4$ is fluoro.

35. 3,7-inter-m-Phenylene-3-oxa-4,5,6-trinor-16,16-difluoro-13,14-dihydro-PGE$_1$, amide, a prostaglandin analog according to claim 34.

36. A prostaglandin analog according to claim 31, wherein R$_3$ and R$_4$ are both hydrogen.

37. A prostaglandin analog according to claim 36, wherein R$_5$ is methyl.

38. 3,7-inter-m-Phenylene-3-oxa-4,5,6-trinor-15-methyl-13,14-dihydro-PGE$_1$, amide, a prostaglandin analog according to claim 37.

39. A prostaglandin analog according to claim 36, wherein R$_5$ is hydrogen.

40. 3,7-inter-m-Phenylene-3-oxa-4,5,6-trinor-13,14-dihydro-PGE$_1$, n-propylamide, a prostaglandin analog according to claim 39.

41. 3,7-inter-m-Phenylene-3-oxa-4,5,6-trinor-13,14-dihydro-PGE$_1$, ethylamide, a prostaglandin analog according to claim 39.

42. 3,7-inter-m-Phenylene-3-oxa-4,5,6-trinor-13,14-dihydro-PGE$_1$, methylamide, a prostaglandin analog according to claim 39.

43. 3,7-inter-m-Phenylene-3-oxa-4,5,6-trinor-13,14-dihydro-PGE$_1$, amide, a prostaglandin analog according to claim 39.

* * * * *

UNITED STATES PATENT OFFICE
CERTIFICATE OF CORRECTION

Patent No. 4,207,257                         Dated  10 June 1980

Inventor(s)   Walter Morozowich

It is certified that error appears in the above-identified patent and that said Letters Patent are hereby corrected as shown below:

Column 2, lines 48-55,

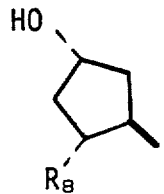     should read     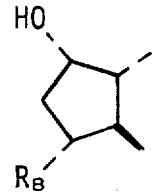

Column 2, line 60 and line 65, "PGF$_1$" should read -- PGF$_1\alpha$ --;
Column 3, lines 47-52,

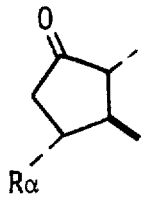     should read     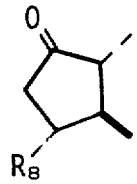

Signed and Sealed this

Seventh Day of April 1981

[SEAL]

Attest:

RENE D. TEGTMEYER

Attesting Officer    Acting Commissioner of Patents and Trademarks